United States Patent [19]
Merk et al.

[11] Patent Number: 5,681,986
[45] Date of Patent: Oct. 28, 1997

[54] ACOUSTIC SENSING

[75] Inventors: John Merk, Winchester; David R. Day, Boxford; Robert E. Newton, Tewksbury, all of Mass.

[73] Assignee: Auburn International, Inc., Danvers, Mass.

[21] Appl. No.: 643,932

[22] Filed: May 7, 1996

[51] Int. Cl.⁶ .................................................. G01N 15/00
[52] U.S. Cl. ............... 73/61.75; 73/861.73; 73/152.18; 310/337; 128/662.03; 367/180
[58] Field of Search ............... 73/54.41, 61.45, 73/61.49, 61.75, 61.79, 64.42, 64.53, 592, 661, 768, 778, 861.18, 702, 861.04, 861.73, 152.18; 128/662.03, 662.06; 310/334, 337; 367/157, 140, 141, 159, 162, 180

[56] References Cited

U.S. PATENT DOCUMENTS

| | | | |
|---|---|---|---|
| 3,816,773 | 6/1974 | Baldwin et al. | 310/319 |
| 3,841,144 | 10/1974 | Baldwin | 73/61 R |
| 4,073,193 | 2/1978 | Mastandrea | 73/432 PS |
| 4,114,063 | 9/1978 | Nelkin et al. | 310/334 |
| 4,131,815 | 12/1978 | Boatright | 310/323 |
| 4,149,415 | 4/1979 | Harbour | 73/432 PS |
| 4,315,428 | 2/1982 | Stuivenwold et al. | 73/61 R |
| 4,607,254 | 8/1986 | Carlson | 340/606 |
| 4,674,337 | 6/1987 | Jonas | 73/861.73 |
| 4,727,750 | 3/1988 | Yonemura | 73/46 |
| 4,838,070 | 6/1989 | Bradley | 73/1 DV |
| 5,301,540 | 4/1994 | Pilacinski et al. | 73/54.24 |
| 5,492,014 | 2/1996 | Hazony | 73/644 |

FOREIGN PATENT DOCUMENTS

| | | |
|---|---|---|
| 969196 | 10/1982 | U.S.S.R. |
| 1 384 882 | 2/1975 | United Kingdom. |
| 1 435 972 | 5/1976 | United Kingdom. |
| WO 93/02808 | 2/1993 | WIPO. |

*Primary Examiner*—Michael Brock
*Assistant Examiner*—Richard A. Moller
*Attorney, Agent, or Firm*—Testa, Hurwitz & Thibeault, LLP

[57] ABSTRACT

An improved invasive acoustic sensor apparatus detects particulate matter in a flow by impingement thereon. The apparatus includes an axially extending probe body having an active length positionable in a flow and a distributed piezoelectric transducer disposed therein. The transducer is acoustically coupled to an interior surface of the body, along substantially the entire active length thereof, and may be a piezoelectric film, piezoelectric tube, or a plurality of electrically parallel connected piezoelectric tube elements. The apparatus further includes an acoustic isolation layer disposed between the probe body and positioning structure to reduce transmission of process wall vibration to the transducer.

12 Claims, 3 Drawing Sheets

5,681,986

1

ACOUSTIC SENSING

TECHNICAL FIELD

The present invention relates to industrial sensors and more particularly to an improved sensor apparatus for detection of particulate in a flow.

BACKGROUND INFORMATION

In a variety of industrial applications as diverse as oil and gas production, power plant operation, and agricultural grain processing, it is often desirable to know of the existence and magnitude of particulate matter entrained in a flow. Such knowledge may be useful, for example, to detect the occurrence of process drift, the presence of contaminants in the process stream, or the occurrence of component malfunction or failure. Sensors have been developed which employ a piezoelectric crystal acoustically coupled to a probe or to a plate extending into a flow. Kinetic impacts of particulate matter on the probe or plate create traveling acoustic waves therein which cause the crystal to produce an electrical output signal which is a function of the acoustic energy produced by the impinging particles. The output signal waveform may be amplified, filtered, and analyzed to predict, for example, the number, size, mass, mass flow rate, momentum, or kinetic energy of the entrained matter.

A fundamental problem with conventional sensors and related prediction methods is the inaccuracy associated therewith, especially when these invasive sensors are employed in industrial process piping. In a typical application, a solid cylindrical probe passes through an aperture in a sidewall of the piping or is disposed in one leg of a tee fitting so that a distal end portion of the probe is immersed in the flow. As particles strike the probe, acoustic waves travel to a piezoelectric crystal mounted at a proximal end of the probe, external to the flow, which converts the acoustic energy to an electrical output signal. Testing has demonstrated that piezoelectric crystal output varies meaningfully as a function of the axial location of impingement on the probe. In other words, a strike at the far distal end of the probe will produce a lower output signal than an equivalent energy strike nearer the proximal end where the piezoelectric crystal is mounted. Accordingly, significant predictive errors inherently will occur depending, for example, on the particulate density distribution profile in the piping at the plane of the probe, as well as the orientation, penetration, and configuration of the probe. Accuracy of the probe is therefore compromised by measurement of the acoustic waves at solely one discrete location, namely the proximal end of the probe.

Further, such sensor installations often entail welding or threadedly engaging the probe to the piping, thereby acoustically coupling the probe to acoustic vibrations occurring in the piping itself. These piping vibrations may result from process flows and particulate impingement on the piping wall itself, especially on angled fittings such as elbows. Further, transmission of resonances and other vibration from motors, pumps, bearings, and rotating equipment connected to the piping can also be detected. Attempts to isolate the acoustic signal induced by particulate impingement on the probe from the total output signal of the piezoelectric crystal have included the use of one or more additional piezoelectric crystal probes mounted externally on the piping wall. The outputs from these additional noninvasive probes are subtracted from the invasive probe output in an attempt to yield a representative signal attributable solely to particulate impact on the invasive probe. Such techniques are both costly and add complexity to the installation of the sensor and signal processing requirements.

Another type of invasive probe is employed in deep well applications where it is impractical to use a solid probe of the aforementioned variety. These well probes are lowered down the borehole to detect depth at which sand and other particulates flow into the borehole and include an annular ring loosely retained between end caps. A piezoelectric crystal is disposed in an interior portion of the ring to signal particulate impact on the ring by a change in output thereof. As with the solid probe, the location of impingement relative to the location of the crystal can be expected to affect the output signal. In order to distinguish between particulate impingement and other extraneous acoustic waves such as those attributable to gas bubbles in a two phase flow, a second ring with an external acoustic damping layer may be employed with a respective piezoelectric crystal. The output of the damped ring crystal may be analytically subtracted from that of the undamped ring crystal to yield a signal indicative solely of particulate impingement. Such techniques, however, do not address the fundamental inaccuracy associated with measuring the acoustic waves at solely one discrete location on the ring.

SUMMARY OF THE INVENTION

An improved acoustic sensor apparatus is disclosed for use generally in any application in which conventional invasive probes are presently employed. The apparatus includes a hollow probe body configured to be substantially fully disposed in a flow stream. A continuous, distributed piezoelectric transducer is disposed in the hollow body such that the transducer is acoustically coupled to an interior surface of the body over substantially the entire length exposed to the flow stream. Accordingly, particulate impacts are actively measured along the entire exposed length of the probe, not merely at a remote location. For a cylindrical probe body, the transducer may be a piezoelectric film, a piezoelectric ceramic crystal tube, or a plurality of piezoelectric ceramic crystal tube elements electrically connected in parallel. In each case, the transducer is configured to geometrically conform to the probe body interior surface. Any voids and interstices may be filled with suitable potting. As a result, inaccuracy resulting from the axial location of impact of particulate matter on the probe body is substantially eliminated.

The sensor apparatus may further include an acoustic isolation layer disposed between the probe body at one end thereof and structure for mounting the probe body relative to the piping or process wall which bounds the flow. Accordingly, sensor output is substantially a function solely of particulate impingement on the body without additional spurious acoustic waves which would otherwise have to be analytically subtracted to yield a useful signal.

BRIEF DESCRIPTION OF THE DRAWINGS

The invention, in accordance with preferred and exemplary embodiments, together with further advantages thereof, is more particularly described in the following detailed description taken in conjunction with the accompanying drawings in which.

DESCRIPTION

Figure 1:
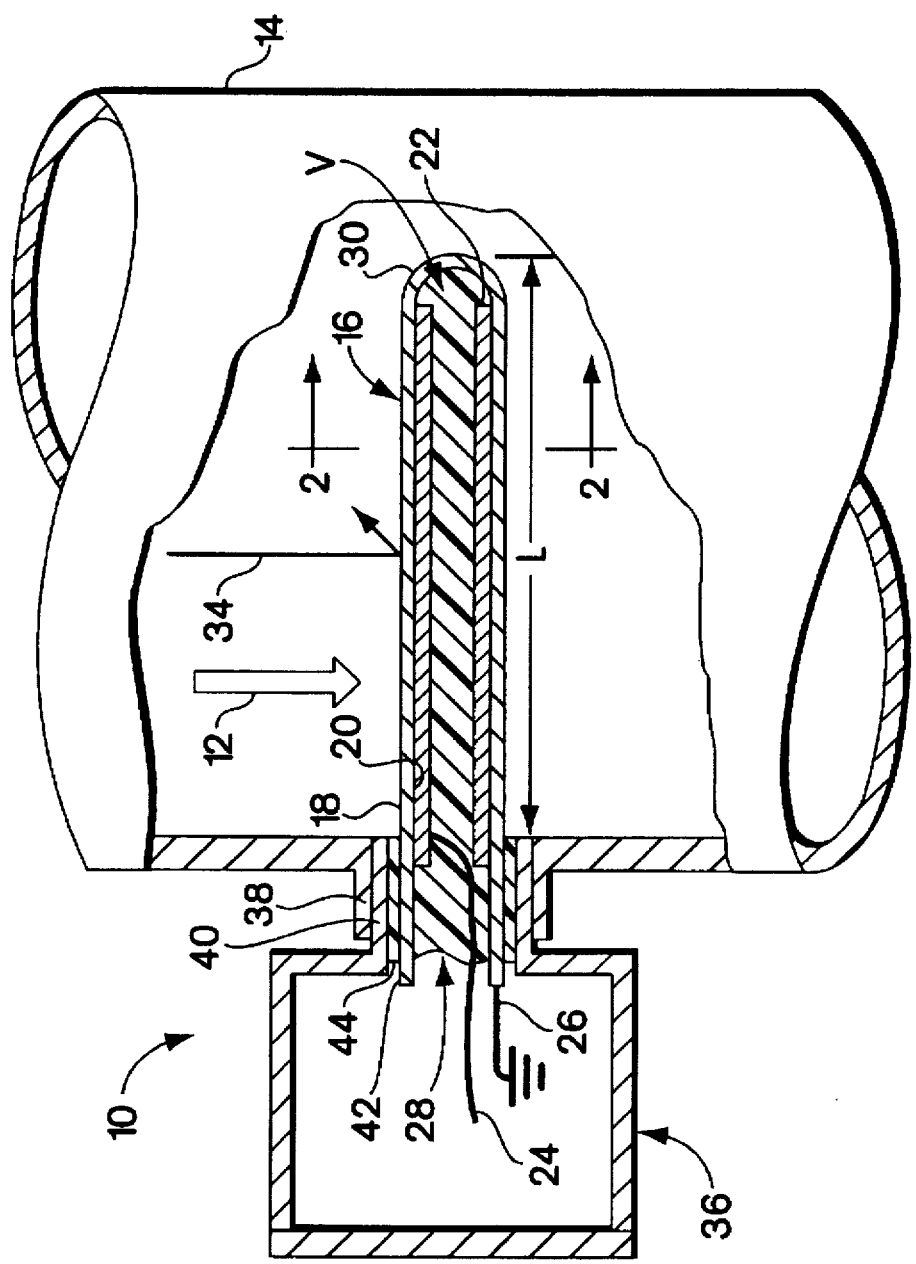
FIG. 1 is a schematic, sectional side view of an apparatus for sensing particulate matter entrained in a flow in a partially broken away pipe in accordance with one embodiment of the present invention.

Depicted in FIG. 1 is a schematic, sectional side view of a sensor apparatus 10 for sensing particulate matter entrained in a flow 12 in a partially broken away pipe 14 in accordance with one embodiment of the present invention. As will be readily apparent to those skilled in the art, advantageous operation of the invention is not limited to the specific elements depicted and the scope of the invention is meant to include all variants, equivalents, and alternative embodiments which rely on the inventive concepts disclosed herein.

The sensor 10 includes a hollow probe body 16 having an axial length, L, at least partially positionable in the flow 12. The probe body 16 has an active exterior surface 18 exposed to the flow 12 and an interior surface 20, which defines a interior volume, V, isolated from the flow 12. Disposed within the probe body 16 is a piezoelectric transducer such as piezoelectric film 22 which is acoustically coupled to the interior surface 20 along substantially the entire active axial length L. Intimate coupling may be achieved by a variety of means, for example by permanent, bonding with a thin layer of epoxy resin. As discussed in greater detail with respect to FIG. 6 hereinbelow, the transducer may be provided with a first metal conductor and an associated electrical lead 24 for attachment to measurement circuitry (not depicted) and a second metal conductor and an associated electrical ground lead connected to the probe body 16 or sensor circuitry electrical ground, shown generally at 26. The remaining void in the hollow probe body 16 may be filled with a suitable potting material 28.

Figure 2:
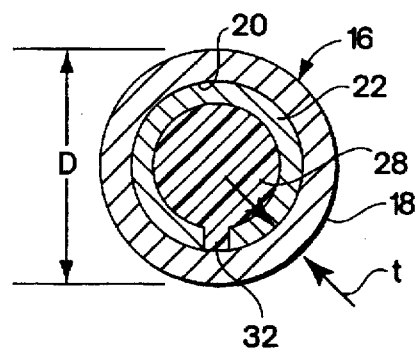
FIG. 2 is an enlarged schematic, cross-sectional view of the apparatus of FIG. 1 taken along line 2—2 in accordance with an embodiment of the present invention.

With reference now also to FIG. 2, wherein is depicted an enlarged schematic, cross-sectional view of the sensor apparatus 10 of FIG. 1 taken along line 2—2, the probe body 16 forms a generally cylindrical shell with a closed arcuate end portion 30. A generally rectangular strip of piezoelectric film 22 may be rolled into the suitable contour and bonded to the interior surface 20 along substantially the entire circumferential extent. A small gap 32 in the film 22 may be placed advantageously within a downstream sector portion of the body 16 where it is unlikely a particulate impact will occur. Routine impacts occur on an upstream sector portion, as illustrated in FIG. 1 with reference to particulate impact shown generally at 34.

The relative thicknesses and dimensions depicted herein are merely for illustrative purposes, actual dimensions being determined to suit a particular application. Variables to be considered may include, for example, the diameter of and pressure within the pipe 14; the distribution, density, and size of particulate matter in the flow 12; and the material of the probe body 16. In an exemplary embodiment, a probe body 16 manufactured from grade 316 stainless steel may have an outer diameter D of between about 0.6 cm and 2.5 cm, an exposed active length L of between about 1 cm and 30 cm, and a wall thickness, t, of between about 0.09 cm and 0.13 cm. Clearly, other materials and dimensions may be employed as desired to suit a particular application. A thin layer of tungsten carbide or other wear coating may be deposited on the exterior surface 18 for use in abrasive flow environments. Suitable protective coatings may also be employed in caustic and acidic flow environments.

The piezoelectric film 22 may be a polyvinylidene fluoride (PVDF), such as that sold under the trade name Kynar, available from Amp Sensors of Valley Forge, Pa., and the bond to the interior surface 20 formed with an epoxy resin such as a typical fast setting, five minute epoxy available from Hardman, Inc. of Belleville, N.J. This resin may also be used advantageously as the potting material 28 to fill the body 16. Other material for bonding includes most epoxies and generally any rigid adhesive capable of maintaining intimate contact and acoustic coupling between the bonded elements for anticipate temperature and mechanical strain cycles. Potting may employ the same materials or alternatively soft cure materials such as silicone rubbers.

Figure 4:
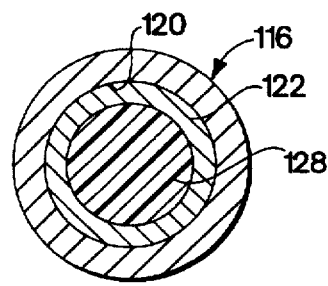
FIG. 4 is an enlarged schematic, cross-sectional view of the apparatus of FIG. 3 taken along line 4—4 in accordance with an embodiment of the present invention.
Figure 3:
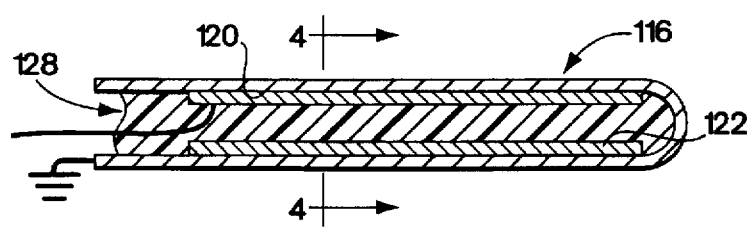
FIG. 3 is a schematic, partially sectional side view of a portion of an apparatus for sensing particulate matter entrained in a flow in accordance with an alternate embodiment of the present invention.

Instead of employing a piezoelectric film 22, alternative piezoelectric materials may be used in accordance with the teachings herein to achieve the desired continuous, distributed piezoelectric transducer of the present invention. For example, shown in FIG. 3 is a schematic, partially sectional side view of hollow, cylindrical probe body 116 in accordance with an alternate embodiment utilizing a piezoelectric ceramic crystal tube 122. FIG. 4 is an enlarged schematic, cross-sectional view of the probe body 116 of FIG. 3 taken along line 4—4 thereof. The size and external configuration of the tube 122 substantially matches the interior volume of the cylindrical probe body 116 with slight radial clearance; however, any clearance, interstices, or deviations therebetween are filled with suitable bonding or potting material 128 which acts to bond the tube 122 to interior surface 120 of the body 116 along substantially the entire active axial length. In a typical application according to the probe dimensions discussed hereinabove with respect to FIG. 1, the clearance is 0.1 cm or less, preferably less than 0.1 cm.

The piezoelectric ceramic crystal tube 122 may be lead zirconate titanate, such as that sold under the trade name PZT-5A, available from Morgan Matroc of Bedford, Ohio, and the bond to the interior surface 120 formed with an epoxy resin such as that discussed hereinabove with respect to bonding piezoelectric film 22 to probe interior surface 20. These bond resins may also be used advantageously as the potting material 128 to fill the body 116.

Figure 5:
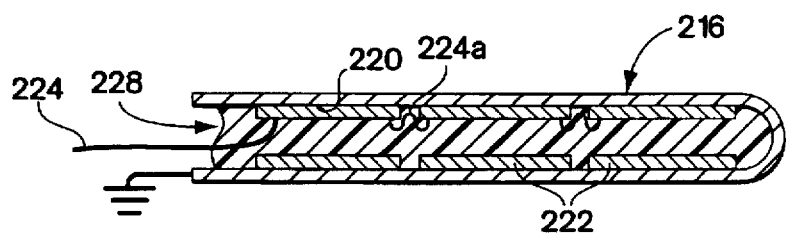
FIG. 5 is a schematic, partially sectional side view of a portion of an apparatus for sensing particulate matter entrained in a flow in accordance with another alternate embodiment of the present invention.

Yet another alternative distributed piezoelectric transducer is depicted in FIG. 5, which shows a schematic, partially sectional side view of hollow, cylindrical probe body 216 utilizing a plurality of electrically parallel connected piezoelectric ceramic crystal tube elements 222. The size, number, and configuration of the tube elements 222 substantially match the interior volume of the cylindrical probe body 216 with slight radial clearance. Any axial interstices between the elements 222 as well as radial clearance or deviations between the elements 222 and the interior surface 220 of the probe body 216 are filled with suitable bonding or potting material 228 which acts to bond the tube elements 222 to the body 216 along substantially the entire active axial length thereof. Parallel electrical signal connections between proximate elements 222 are afforded by a number of interdisposed electrical signal leads 224a and corresponding ground leads. The greater the number of elements 222 employed, the greater the ability of the probe 216 to deflect without damaging the crystals. Since the entire probe 216 is filled with potting material 228, it is contemplated that the increased number of electrical connections required in this embodiment will not substantially compromise the reliability thereof. The piezoelectric ceramic crystal tube elements 222 may be lead zirconate titanate similar to that employed in the embodiment depicted in FIGS. 3 and 4 hereinabove. Similar bonding and potting materials and techniques may also be employed.

Figure 6:
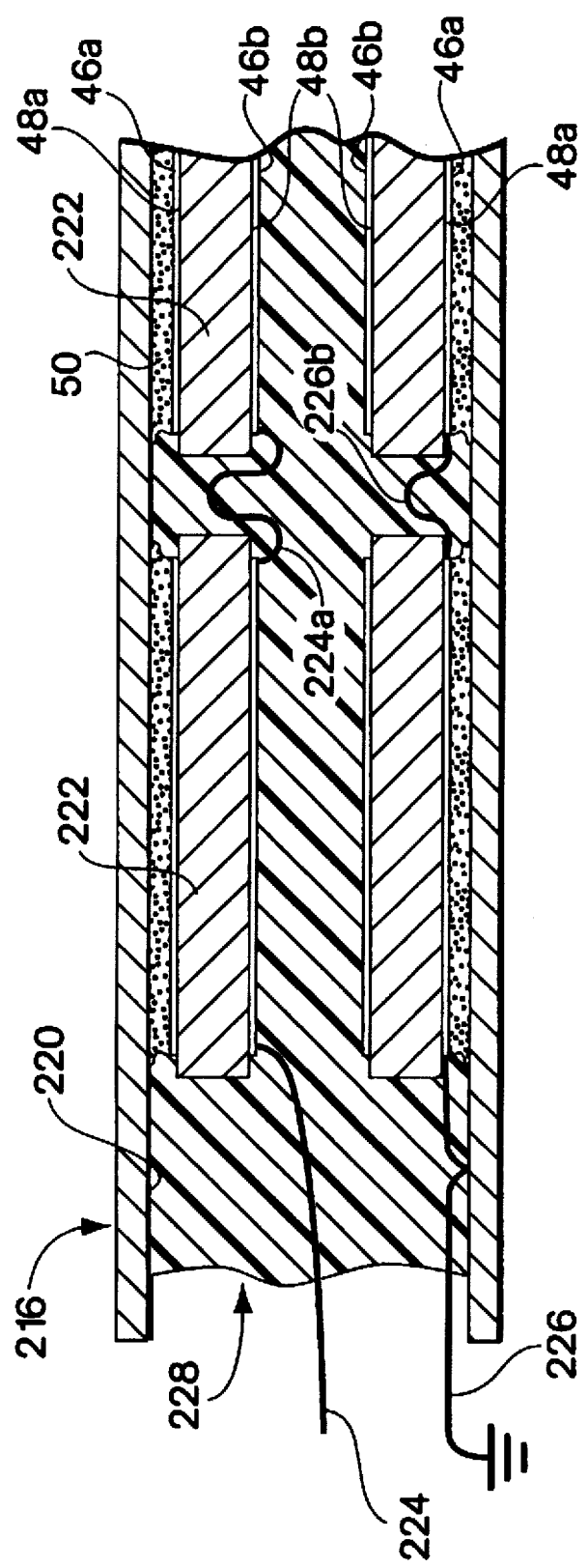
FIG. 6 is an enlarged schematic view of a portion of the apparatus of FIG. 5 in accordance with an embodiment of the present invention.

To facilitate fabrication, typical piezoelectric transducers are produced with metallic films 46a, 46b on opposed major surfaces 48a, 48b to provide for electrical connection thereto, as depicted in an enlarged schematic view in FIG. 6 of a portion of the probe body 216 depicted in FIG. 5. Depending on the manufacturer of the transducer, electrical signal and ground lead wires 224, 226 may or may not be attached to the films 46a, 46b. If none are provided, lead wires may be attached readily by soldering or by using a conductive adhesive.

During fabrication of the probe 216 according to the invention, one major surface 48a of each piezoelectric tube element 222 is oriented proximate the probe interior surface 220 and bonded thereto with a layer of epoxy, potting, or other suitable adhesive material, shown generally at 50. The thickness of the adhesive 50 is shown in an exaggerated manner to facilitate depiction. Surfaces 48a are collectively defined as the ground side of the transducer. A reliable connection to ground may be accomplished, as depicted, by a plurality of interdisposed electrical leads 226a linking proximate ground side films 46a, in combination with a single lead 226 attached to a ground lug or other suitable connection (not depicted) in the wiring enclosure 36. The probe body 216 may also be attached to ground and alternatively may provide a common ground connection for each tube element ground side film 46a with direct connection thereto at each element 222, if desired.

The major surfaces 48b of the tube elements 222 oriented away from the probe interior surface 220, that is the films 46b oriented toward the centerline of the probe body 216, are collectively defined as the signal side of the transducer. A plurality of interdisposed electrical leads 224a may be used to link proximate signal side films 46b. Electrical lead 224, attached to one such signal side film 46b, may be attached to the measurement electronics for signal amplification and processing. Accordingly, the tube elements 222 are electrically connected in parallel. In other words, the ground side films 46a are connected one to the next and ultimately to ground via lead 226. Similarly, the signal side films 46b are connected one to the next and ultimately to the measurement electronics via lead 224.

As may be appreciated readily by those having skill in the art, similar electrical connections between transducers, measurement electronics, and ground may be provided for flexible piezoelectric film 22 of probe body 16 and piezoelectric tube 122 of probe body 116, although there is no need for interdisposed leads 224a, 226a since these embodiments employ solely a single continuous piezoelectric film or crystal.

Referring again to FIG. 1. The sensor apparatus 10 further includes a wiring enclosure 36 for providing electrical connections to signal processing circuitry, some of which may be disposed therein, such as filter and amplifier circuits. The enclosure 36 may also include means for positioning or mounting the probe body 16 relative to the pipe 14 or other process wall bounding the flow 12. In the particular embodiment depicted, the pipe 14 has an internally threaded port 38 and the enclosure 36 a mating externally threaded nipple 40 for reliably coupling the apparatus 10 to the pipe 14. Any of a variety of conventional mating coupling elements may be employed, such as bolted flanges or bayonet retention devices. Regardless of the positioning means employed, acoustic isolation of the probe body 16 therefrom is desirable. Accordingly, disposed between the nipple 40 and a proximal end 42 of the probe body 16 is an annular, axially extending layer of compliant material 44. The compliant material 44 may be potting, sufficiently tough to reliably retain the probe body 16 while sufficiently compliant to acoustically isolate the body 16 from pipe vibrations passing through the threaded connection. A silicon rubber potting compound such as that sold under the trade name P-50, available from Silicones, Inc. of Highpoint, N.C., has been found to exhibit the desired properties. The layer 44 may extend substantially fully along the overlapping axial length of the probe body 16 and nipple 40 and may be between about 0.05 cm and 1.0 cm in radial thickness. Any of the probes 16, 116, 216 may be used in combination with the acoustic isolation feature of the enclosure 36 to achieve the desired result.

While the piezoelectric transducers and associated potting materials disclosed herein may be used in flow environments up to about 100° C. and provide exemplary frequency response between about 10 KHz and 500 KHz, these values and ranges can be increased for applications in harsh environments. For example, through the use of more heat tolerant ceramic piezoelectric crystals and appropriate potting, sensors 10 according to the teachings herein may be used in flow environments up to about 300° C. or greater. Further, if desired, the frequency range may extend from DC to 10 MHz or higher.

While there have been described herein what are to be considered exemplary and preferred embodiments of the present invention, other modifications of the invention will become apparent to those skilled in the art from the teachings herein. For example, while it is advantageous to manufacture the tube body 16 as a cylindrical element to reduce disruption to the flow 12, as well as provide structural stability, other shapes may be employed as desired including those having contoured cross-sections such as those which are oval, ellipsoidal, and airfoil shaped, and those with prismatic cross-sections such as those which are triangular, rectangular, and polygonal. In each case, the probe body includes a continuous, distributed piezoelectric transducer extending substantially along the entire active axial length of the body subject to the flow. If desired, however, the transducer may extend solely along a limited axial extent of the body exposed to the flow, to reduce the active length thereof. Such a configuration may be employed in the case where particulate matter location in the flow is predictable or where solely detection of particulate matter in a limited portion of the flow area is of primary interest. In the latter case, the remainder or inactive length of the probe may be shielded with an external acoustic damping layer, if desired, to effectively prevent generation of acoustic waves in the probe due to particulate impacts along the inactive length thereof.

The sensor apparatus 10 may be used in a broad variety of commercial and industrial applications, generally wherever conventional invasive probes are presently utilized, including borehole applications where well probes are Used. In such instances, a piezoelectric film may be acoustically coupled by bonding to a bore of the captured annular ring substantially along its entire circumferential and axial directions.

It is therefore desired to be secured in the appended claims all such modifications as fall within the true spirit and scope of the invention. Accordingly, what is desired to be secured by Letters Patent is the invention as defined and differentiated in the following claims.

We claim:

1. A sensor apparatus for measuring acoustic energy produced by impingement of particulate thereon, said apparatus comprising:

a probe body including:

an exterior surface having an active axial length positionable in a flow; and an interior surface defining an interior volume of said probe body; and a piezoelectric transducer disposed within said interior volume and acoustically coupled to said interior surface along substantially said active axial length.

2. The invention according to claim 1 wherein said piezoelectric transducer comprises piezoelectric film bonded to said interior surface.

3. The invention according to claim 1 wherein said piezoelectric transducer comprises a piezoelectric ceramic crystal bonded to said interior surface.

4. The invention according to claim 3 wherein:

said probe body comprises a generally cylindrical shell; and said piezoelectric ceramic crystal is configured as a tube.

5. The invention according to claim 1 wherein said piezoelectric transducer comprises a plurality of electrically parallel connected piezoelectric ceramic crystal elements bonded to said interior surface.

6. The invention according to claim 5 wherein:

said probe body comprises a generally cylindrical shell; and said piezoelectric ceramic crystal elements are configured as a plurality of substantially similar tubes.

7. The invention according to claim 1 further comprising potting disposed within said interior volume to fill substantially said interior volume.

8. The invention according to claim 1 further comprising means for positioning said probe body in the flow wherein said positioning means is acoustically isolated from said probe body.

9. The invention according to claim 8 wherein a layer of potting is disposed between said positioning means and said probe body.

10. The invention according to claim 8 wherein said positioning means comprises a mate to a process wall coupling element.

11. The invention according to claim 10 wherein said apparatus further comprises a wiring enclosure attached to said mate.

12. The invention according to claim 1 wherein said piezoelectric transducer includes an electrical ground connection to said probe body.

* * * * *